United States Patent [19]

Kulla et al.

[11] Patent Number: 4,605,564

[45] Date of Patent: Aug. 12, 1986

[54] COATING PROCESS FOR MAKING ANTIMICROBIAL MEDICAL IMPLANT DEVICE

[75] Inventors: James P. Kulla, Perrysburg; Norman J. Huff, Swanton, both of Ohio

[73] Assignee: Biological & Environmental Control Laboratories, Inc., Toledo, Ohio

[21] Appl. No.: 572,744

[22] Filed: Jan. 23, 1984

[51] Int. Cl.$^4$ .............................................. A01N 1/02
[52] U.S. Cl. ............................................ 427/2; 424/16; 427/232; 427/384; 604/265
[58] Field of Search ................ 424/16, 347; 427/2, 427/232, 384; 604/264, 265

[56] References Cited

U.S. PATENT DOCUMENTS

| | | | |
|---|---|---|---|
| 2,880,129 | 3/1959 | Billings | 427/2 |
| 3,566,874 | 3/1971 | Shepherd et al. | 604/265 |
| 3,604,426 | 9/1971 | Erickson | 604/265 |
| 4,081,267 | 3/1978 | Hashimoto et al. | 427/249 |
| 4,318,907 | 3/1982 | Kligman et al. | 424/230 |
| 4,355,028 | 10/1982 | Kligman et al. | 424/230 |
| 4,381,380 | 4/1983 | Le Veen et al. | 604/265 |
| 4,500,339 | 2/1985 | Young et al. | 427/2 |

*Primary Examiner*—John F. Niebling
*Assistant Examiner*—Terryence Chapman

[57] ABSTRACT

The invention relates to an antimicrobial medical implant device having a chlorinated phenol impregnated therein, such as para-chloro-meta-xylenol.

4 Claims, No Drawings

COATING PROCESS FOR MAKING ANTIMICROBIAL MEDICAL IMPLANT DEVICE

BACKGROUND OF THE INVENTION

This invention relates in general to antimicrobial techniques and, in particular, to an antimicrobial medical implant device.

More specifically, but without restriction to the particular use which is shown and described, the invention relates to an antimicrobial medical implant device having a chlorinated phenol impregnated therein, such as parachloro-meta-xylenol.

The use of catheters in humans and animals is widespread in the treatment of countless diseases and conditions. The presence of catheters, however, generally involves the risk of bacterial and mycotic contamination and sepsis. An example of one type of catheter in which the problem of bacterial or other infection is prevalent is the well-known Foley catheter.

It has been found that patients, in whom a Foley catheter is implanted for more than several days, encounter a substantial risk of bladder infection. When catherized, such patients undergo a steady urine drip. As the urine is collected in the conventional manner, bacteria travel along the channel of the catheter back into the patient. The possibility of migration of bacteria and the like along the exterior route of the catheter is also possible. In the past, catheters have been coated with various antimicrobial substances, but such known techniques are generally ineffective over extended periods of time.

SUMMARY OF THE INVENTION

It is an object of this invention to provide an improved antimicrobial material.

Another object of this invention is to provide an antimicrobial medical implant device.

A further object of the invention is to impregnate a catheter or other implant with antimicrobial chlorinated phenols.

Still another object of this invention is to impregnate a catheter or other implant with a chlorinated phenol from 0.1% to 10% (wt/wt).

A still further object of this invention is to provide an improved method of impregnating a medical grade polymer with an antimicrobial agent.

These and other objects are attained in accordance with the present invention wherein there is provided an improved antimicrobial medical implant device such as a catheter intended for use in humans and incorporating a means for preventing infection. The catheter is impregnated with a chlorinated phenol, such as a para-chloro-meta-xylenol sold under the trademark Ottasept ®. The impregnated catheter or implant of the invention is capable of extended antimicrobial activity and is relatively non-toxic. The antimicrobial implant of the invention is capable of superior prevention of the risk of contamination arising by virtue of a catheter or similar implant polymer within a human patient. Para-chloro-meta-xylenol is only slightly soluble in water (1 part in 3,000 parts) and aqueous body fluids. Thus, the ingredient remains active in the treatment and prevents infection for a greater period of time than other more soluble infection fighting compounds. These beneficial properties, which heretofore have not been taken advantage of in the prior art, are incorporated in the polymer of the implant device to accomplish the improved results of the invention.

DESCRIPTION OF THE INVENTION

This invention comprises the impregnating of a chlorinated phenol from 0.1% to 10% (wt/wt) into a latex, polymer, or other material intended for use in humans as a means of preventing infection. The invention of the application reduces or eliminates the risk of contamination in the presence of a medical implant and particularly is effective in connection with a well-known latex Foley catheter. The technique of impregnation herein disclosed is also advantageous in connection with other devices including, but not limited to, peritoneal-dialysis catheters (silicone or other polymers), intravenous catheters (polyurethane), ventricular shunts, arterio-venous shunts, fistula sets and other implants of latex or polymers. In addition, accessories attached to catheters and implants can likewise be impregnated with chlorinated phenols to further reduce infection risk, e.g. urine drain bags.

Although other chlorinated phenols may be used in accordance with the invention, it is found that para-chloro-meta-xylenol sold under the trademark Ottasept is highly effective. Para-chloro-meta-xylenol is particularly suitable, because of its low solubility and can be effectively impregnated into a latex or polymer. Para-chloro-meta-xylenol further has very broad bactericidal-fungicidal properties in low concentrations through a wide range of pH. Thus, para-chloro-meta-xylenol acts as an active ingredient while impregnated in latex or a polymer for extended periods of time in comparison to more soluble compounds known for use in treating or preventing infections. In addition, the compound has a long history of safe applications, is stable at room temperature, and is not readily absorbed by proteins.

Para-chloro-meta-xylenol has several synonyms including 3,5-dimethyl-4-chlorophenol, 2-chloro-m-5-xylenol, and 2,6-dimethyl-4-hydroxchlorobenzene. Para-chloro-meta-xylenol is impregnated into the latex (or other polymers) of a device by using an appropriate solvent, such as a chlorinated solvent. Other materials may require an alcohol solvent. A latex Foley catheter containing para-chloro-meta-xylenol (at 0.1%–10%) would reduce or eliminate the risk of contamination via the routes of insertion, along the outside of the catheter (catheter/urethral interface) or through the lumen of a catheter.

To impregnate a latex Foley catheter, the implant is immersed in a solution of 1%–6% para-chloro-meta-xylenol in dichloromethane. The dichloromethane causes considerable swelling of the latex. After immersion of the latex for approximately ninety minutes, the catheter is removed from the solution and allowed to dry at room temperature, during which time the latex returns to its original size. After drying, the latex catheter is rinsed for approximately thirty seconds in ethanol (or other alcohol). The resulting catheter is thus impregnated with para-chloro-meta-xylenol.

The invention is directed in general to the treatment of any polymer or latex with an organic solvent, such as dichloromethane or chlorinated ethanes, in which the para-chloro-meta-xylenol is readily soluble and which will also cause swelling of the polymer of interest. The solvent should be readily removable by evaporation or by a series of solvent exchanges with one or more other solvents like alcohol (ethanol) or water, so that the microbial agent, para-chloro-meta-xylenol, is trapped or is precipitated into the polymer structure as the polymer returns to its original size.

In some applications, the antimicrobial agent could be impregnated into a latex, polymer, or a fabric material, e.g. dacron, which is then attached to a device into which a chlorinated phenol is not easily incorporated.

While the invention has been described with reference to the preferred embodiments, it will be understood by those skilled in the art that various changes may be made and equivalents may be substituted for elements thereof without departing from the scope of the invention.

In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A process for making an antimicrobial medical implant device comprising the steps of:
   providing a medical implant device formed of a composition comprising a medical grade polymer or latex;
   treating said polymer or latex with a solution of para-chloro-meta-xylenol having a very low solubility in water and aqueous body fluids, with the para-chloro-meta-xylenol dissolved in an organic solvent to cause swelling of the polymer or latex;
   thereafter removing the solvent from the solution to trap or precipitate the para-chloro-meta-xylenol in the polymer or latex structure;
   whereby the para-chloro-meta-xylenol is impregnated within the structure of the polymer or latex.

2. A process as described in claim 1, wherein the para-chloro-meta-xylenol is 0.1 percent to 10 percent by weight.

3. A process as described in claim 1, wherein said solvent is dichloromethane.

4. A process as described in claim 1, wherein said solvent is carbon tetrachloride.

* * * * *